United States Patent [19]

Marchese et al.

[11] 4,105,023

[45] Aug. 8, 1978

[54] PACEMAKER ARTIFACT SUPPRESSION IN CORONARY MONITORING

[75] Inventors: Thomas F. Marchese, Somerville; Rauf S. Argon, Bedford, both of Mass.

[73] Assignee: American Optical Corporation, Southbridge, Mass.

[21] Appl. No.: 760,487

[22] Filed: Jan. 19, 1977
(Under 37 CFR 1.47)

[51] Int. Cl.² .............................................. A61B 5/04
[52] U.S. Cl. ........................... 128/2.06 B; 128/2.06 F; 128/419 PT
[58] Field of Search ...................... 128/2.06 B, 2.06 G, 128/2.06 R, 2.05 T, 419 PT, 206 F

[56] References Cited

U.S. PATENT DOCUMENTS

| | | | |
|---|---|---|---|
| 3,478,328 | 11/1969 | Schillinger | 128/2.06 R |
| 3,534,282 | 10/1970 | Day | 128/2.06 B |
| 3,651,799 | 3/1972 | Daynard | 128/419 PT |
| 3,923,041 | 12/1975 | Stasz et al. | 128/419 PT |
| 3,986,496 | 10/1976 | Brastad | 128/419 PT |

*Primary Examiner*—Kyle L. Howell
*Assistant Examiner*—Arthur S. Rose
*Attorney, Agent, or Firm*—Jeremiah J. Duggan; Stephen A. Schneeberger

[57] ABSTRACT

In heart monitoring systems for use with patients whose hearts may be stimulated by an artificial pacer and which system includes heat rate indicating means, there is provided circuitry for suppressing the recharge waveform portion of a pacer signal artifact in addition to suppression of the discharge pulse portion of the signal artifact, thereby to prevent inaccuracies in the heart rate indication arising from the pacer signal artifact. In addition to suppressing the discharge pulse portion of a pacer signal artifact with conventional means, the invention recognizes that the recharge waveform of the pacer signal may cause a false impression of a QRS complex which actuates heart rate indicating means and provides novel circuitry for suppressing such recharge waveform.

Circuitry is provided for recognizing the occurrence of a pacer discharge pulse and for generating a suppression signal in timed relation thereto which, when arithmetically added to the recharge waveform portion, acts to cancel or suppress such recharge portion. The suppression signal is of inverse polarity to the recharge waveform portion and is generated by sampling the pacer signal artifact substantially at the beginning of the recharge waveform to determine the magnitude thereof. In a preferred embodiment, a pacer signal artifact and the termination of the discharge pulse portion thereof is identified by novel rate and duration measuring circuitry.

9 Claims, 7 Drawing Figures

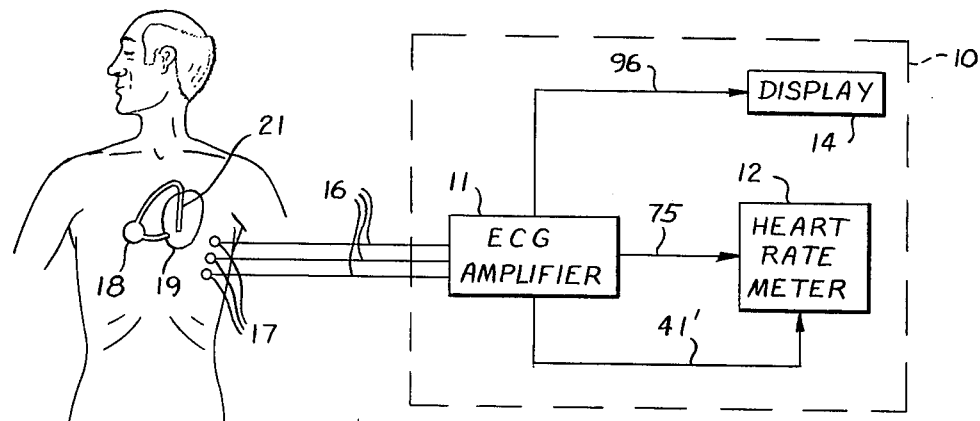
Fig. 1
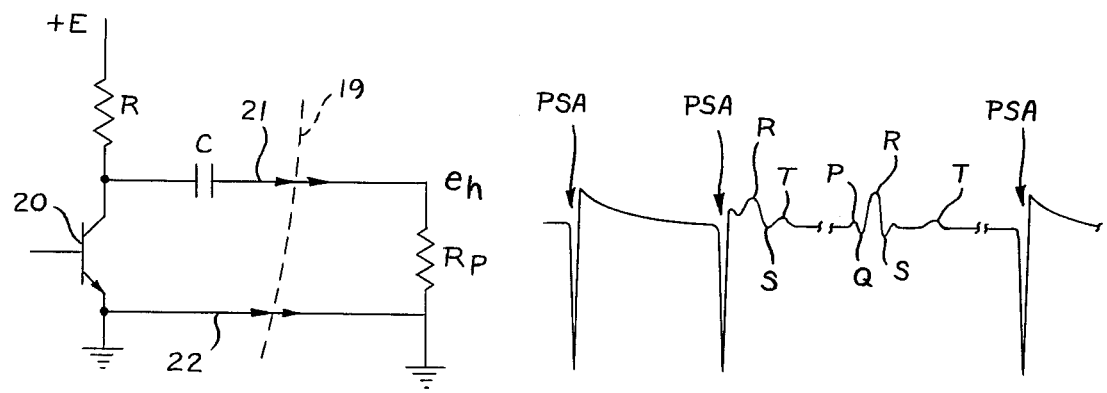
Fig. 2
Fig. 3
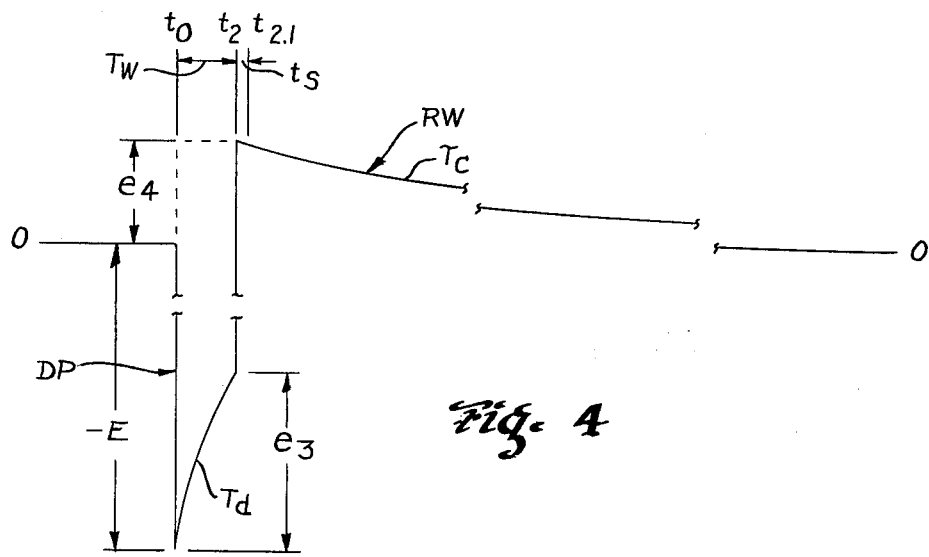
Fig. 4

PACEMAKER ARTIFACT SUPPRESSION IN CORONARY MONITORING

BACKGROUND OF THE INVENTION

The invention relates generally to heart monitoring systems and more particularly to heart rate monitoring systems, particularly in the presence of artificial heart pacer signal artifacts.

In the art of heart monitoring, particularly to determine a patient's heart rate or the like, thoracic electrical potentials of the patient are sensed to provide an input signal to amplifying means which amplify and process the signal for application to heart rate indicating means and/or display means. In the particular instance of heart rate monitoring, the heart rate indicator is normally responsive only to sensed signals which correspond in frequency and amplitude substantially with the QRS complex or the R-wave of a natural heart beat appearing in the ECG. However, in the event the patient is receiving artificial stimulation as by an implanted heart pacer, the pacer's stimulation pulse may additionally introduce signal amplitudes and/or frequencies to the sensed ECG signal which may be inaccurately identified as a naturally occurring heart rhythm and, in the worse case may provide an indication of continuing heart activity when in fact heart activity has ceased and the patient is technically dead.

To avoid the foregoing problem, the prior art has provided various circuit means for suppressing the pacer discharge pulse portion of the pacer signal artifact, usually be preventing transmission of the sensed ECG signal to the heart rate indicating circuitry for the duration of the pacer discharge pulse.

Heart pacers are normally operated such that there is no resultant or net polarization of their electrodes, and thus may be said to operate in an AC mode. The most effective way of accomplishing this AC mode of pacer operation is through capacitively coupling the heart stimulating energy to the heart. However because of such capacitive coupling and AC operation, the main discharge of the energy-storing capacitor to provide the stimulation pulse is followed by a recharge of the capacitor. The recharging capacitor results initially in the sensed ECG exhibiting an overshoot voltage having the opposite polarity to the heart stimulation pulse, which overshoot decays exponentially to a zero voltage value at a rate determined by the time constant of the capacitor recharge path. The resulting recharge voltage or waveform, sometimes known as a pacer "tail," has recently been recognized as having ample amplitude and a frequency spectrum in the domain of the QRS complex such as to be able to trigger or enter a false count on the heart rate monitor.

Accordingly, it is a principle object of the present invention to provide an improved heart monitoring system having heart rate indicating means. Included in this object is the provision of means for preventing false actuation of the heart rate indicating means by any portion of a heart pacer signal artifact.

SUMMARY OF THE INVENTION

In accordance with the principles of the invention, there is provided, in a heart monitoring system including means for sensing a patients ECG signals, means responsive to the QRS complex of sensed ECG signals for indicating the patients heart rate, and signal suppression means for suppressing the pacer discharge pulse portion of a heart pacer signal artifact possibly appearing in the sensed ECG signal and additionally comprising a recharge waveform portion, the improvement wherein the suppression means additionally includes: means responsive to a pacer signal artifact in the sensed ECG signal for generating a recharge waveform suppression signal of opposite polarity to the recharge waveform portion of the pacer signal, and means for arithmetically summing the recharge waveform suppression signal with the sensed ECG signal to additionally suppress the recharge waveform portion, the magnitude and duration of the recharge waveform suppression signal being such as to thereby also prevent false actuation of the heart rate indicating means by the recharge waveform of the pacer signal artifact.

The recharge waveform suppression signal is preferably proportional, and in fact, substantially equal to, the magnitude of the recharge waveform portion of the pacer signal which it seeks to cancel. Further, the duration of the recharge waveform suppression signal is at least sufficient to suppress that initial portion of the recharge waveform which otherwise would be capable of registering a false count in the heart beat indicating means.

The signal suppression circuit means includes means responsive to a pacer signal artifact for generating a strobe signal substantially at the beginning of the recharge waveform portion thereof, and the recharge waveform suppression signal generating means comprises a transient generator providing an output signal the magnitude of which is a function of the magnitude of an input signal applied thereto, and switch means responsive to the strobe signal for extending the beginning of the recharge waveform portion of the pacer signal artifact to the transient generator as the input signal thereto. The recharge waveform portion of the pacer signal artifact is an exponential charging function and the transient generator comprises an RC circuit having parallel-connected resistance and capacitance means connected in series with the switch means and the summing means. Further, the value of the RC circuit is selected to provide an exponential decay of the input signal which, inversely, corresponds substantially with the exponential charging function of the recharge waveform portion of the pacer signal artifact. Means may be provided for variably scaling the magnitude of the generated inverse transient signal.

The strobe signal generating means comprises circuitry for obtaining the time derivative of the sensed ECG signal including any possible pacer discharge pulse, means responsive to the time derivative for providing a trigger signal each time the magnitude of the time derivative exceeds a threshold corresponding with a respective particular minimum slew rate of the sensed signal, there being separate thresholds for the opposite polarities of the time derivative signals selected such that a first trigger signal is provided at the start of a pacer discharge pulse and a second trigger signal is provided at the end of the pacer discharge pulse, and means responsive to the first trigger for initiating a predetermined timing interval following a predetermined delay, the termination of a normal pacer discharge pulse normally occurring during the timing interval, and means responsive to the second trigger occurring during the predetermined interval for generating the strobe pulse. The thresholds for the opposite polarities of the time derivative signals may conveniently be oppositely-signed equal values.

BRIEF DESCRIPTION OF THE DRAWINGS

FIG. 1 is a diagramatic representation of the heart rate monitoring equipment of the invention operatively connected to a patient having an implanted heart pacer;

FIG. 2 depicts the output circuit of the heart pacer including the impedance of the patient;

FIG. 3 represents the sensed thoracic voltage waveform of a patient having a pacemaker and includes sensed pacer stimulation pulses and PQRST complexes of the heart;

FIG. 4 is an enlarged partial view of FIG. 3 showing a sensed pacer signal artifact in greater detail;

DESCRIPTION OF THE PREFERRED EMBODIMENTS

Figure 5:
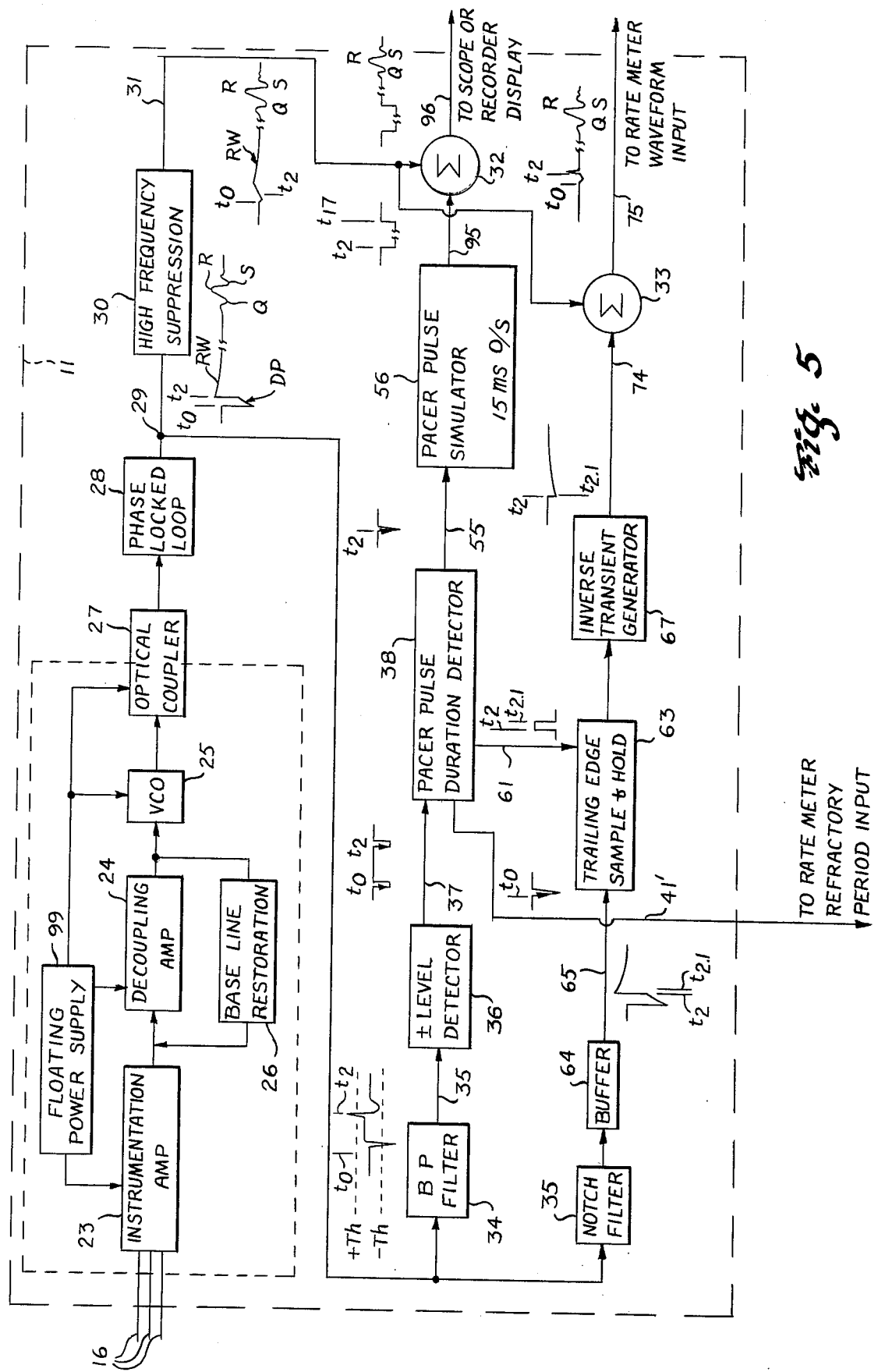
FIG. 5 is a detailed functional block diagram of the ECG amplifier and most of the pacer signal artifact suppression circuitry of the heart rate monitoring system of FIG. 1.

Referring to FIG. 1 there is illustrated a heart rate monitoring system 10 comprised of an ECG amplifier 11 and a heart rate monitor 12, and additionally an optional display 14 which may be a CRT and/or a permanent recorder. The monitoring system 10 and more specifically the ECG amplifier 11, is electrically connected to a patient 15 via a plurality of conductors 16 connected with respective electrodes 17 in contact with, and appropriately positioned on, the skin of the patient.

Patient 15 is illustrated as having an implanted monopolar pacer 18 connected in operative heart stimulating relation with his heart 19. Typically the output circuitry of pacer 18, as illustrated in FIG. 2, includes a capacitor, C, connected through a resistor, R, to a source of voltage, +E, and connected at its other end to a heart electrode 21 which is operatively disposed within or adjacent to heart 19. Another electrode 22 of the pacer 18 is also operatively connected to the heart 19 and serves as a circuit reference or current return path. The patient 15 represents an impedance $R_p$ between the electrodes 22 and 21. Capacitor C charges through the circuit comprising patient impedance $R_p$, capacitor C and resistor R. A switching transistor 20 having a grounded emitter and having its collector connected to resistance R and capacitor C is switched into conduction for discharging the energy stored in capacitor C into the heart 19 to provide stimulation in a known manner.

FIG. 4 represents the waveform of the voltage $e_h$ appearing at electrode 21 of pacer 18 in FIG. 2 during and following the generation of a pacer discharge or stimulation pulse DP. Capacitor C is assumed to be charged to voltage +E prior to the occurrence, at time $t_o$, of a control signal of duration $T_w$ on the base of transistor 20. The control signal (not shown) controls the time during which energy is discharged to the heart 19 and typically may be about 0.5-3 msec., with 2 msec. being selected for the purposes of illustration herein. At $t_o$, transistor 20 conducts, immediately dropping the voltage at electrode 21 by the magnitude E. The capacitor C then begins to discharge through the heart with a time constant $T_d$ which is the product of capacitor C and the patient impedance $R_p$. At the end of 2 msec., normally prior to complete discharge of capacitor C, transistor 20 is turned off and the capacitor C begins to recharge with the time constant $T_c$ being equal to (R + $R_p$) C.

It will be noted in FIG. 4 that when the discharge pulse DP terminates at $t_2$ (2 msec.), the voltage on pacer electrode 21 moves positively beyond the normal zero reference level and experiences an overshoot voltage $e_4$ which is determined by the relationship $e_4 = e_3 R_p/(R + R_p)$, where $e_3$ is the magnitude of voltage decay during discharge of capacitor C. Typically, the magnitude of voltage E may be 6 volts, and the magnitude of the overshoot $e_4$ will be about 1/40 of that, or about 150 mv. The recharge time constant $T_c$ is possibly 200 - 300 msec. such that capacitor C is not substantially fully recharged for possibly 500 msec. or more. Accordingly, it will be appreciated that the pacer recharge waveform RW, or so called pacer "tail," may have a magnitude greater than 100 mv at the heart for many 10's of milliseconds and even more than 100 msec.

Although the magnitude of the pacer discharge pulse DP and the recharge waveform RW are substantially attenuated when sensed by electrodes 17 at the skin of patient 15, the electrical signals attendant normal heart functioning and represented by the PQRST complex of FIG. 3 are similarly attenuated such that the pacer discharge pulse DP is normally many times larger than any part of the PQRST complex and the recharge waveform RW may have an initial magnitude comparable to or greater than the R-wave portion of the complex. Furthermore, the general frequency characteristics of the discharge waveform RW are comparable to those exhibited by a normal QRS complex. For these reasons, the pacer discharge pulse DP and/or the recharge waveform RW may jointly or separately appear as normal QRS complexes to the R-wave detection circuitry of heart rate meter 12.

Referring briefly to FIG. 3, the displayed waveform illustrates the signal sensed by electrode 17 at the skin of patient 15 and provided as an input signal to amplifier 11 of the rate monitoring system 10. The left-most perterbation in the signal is designated PSA for Pacer Signal Artifact and includes the discharge pulse portion DP and the recharge waveform portion RW of a pacer pulse. This particular PSA was not successful in achieving capture of the heart. The next-rightward perterbation shows a pacer signal artifact PSA which was successful in achieving capture of the heart, thus resulting in the stimulated generation of the RST complex by the heart within about 100 msec. after the pacer pulse. Next rightward, there is illustrated a complete, natural PQRST complex of the heart, with no PSA signal in asmuch as pacer 18 is of the demand type. Finally, there is a repetition of a pacer signal artifact PSA which is unsuccessful in achieving capture of the heart.

The heart rate meter 12, to be discussed hereinafter in somewhat greater detail, possesses magnitude and frequency discriminating circuitry of a generally known type for recognizing the R-wave in the ECG signal, and recording or indicating such as evidence of a heart beat. However that circuitry of meter 12 may also respond to the discharge pulse DP and/or the recharge waveform RW of the pacer signal artifact PSA to additionally register at heart beat, when in fact none may be present. Accordingly, circuitry associated with amplifier 11 and the front end of rate meter 12 is operative to suppress not only the discharge pulse DP but also the recharge waveform RW in accordance with the invention to prevent their falsely actuating the rate meter 12.

Figure 6:
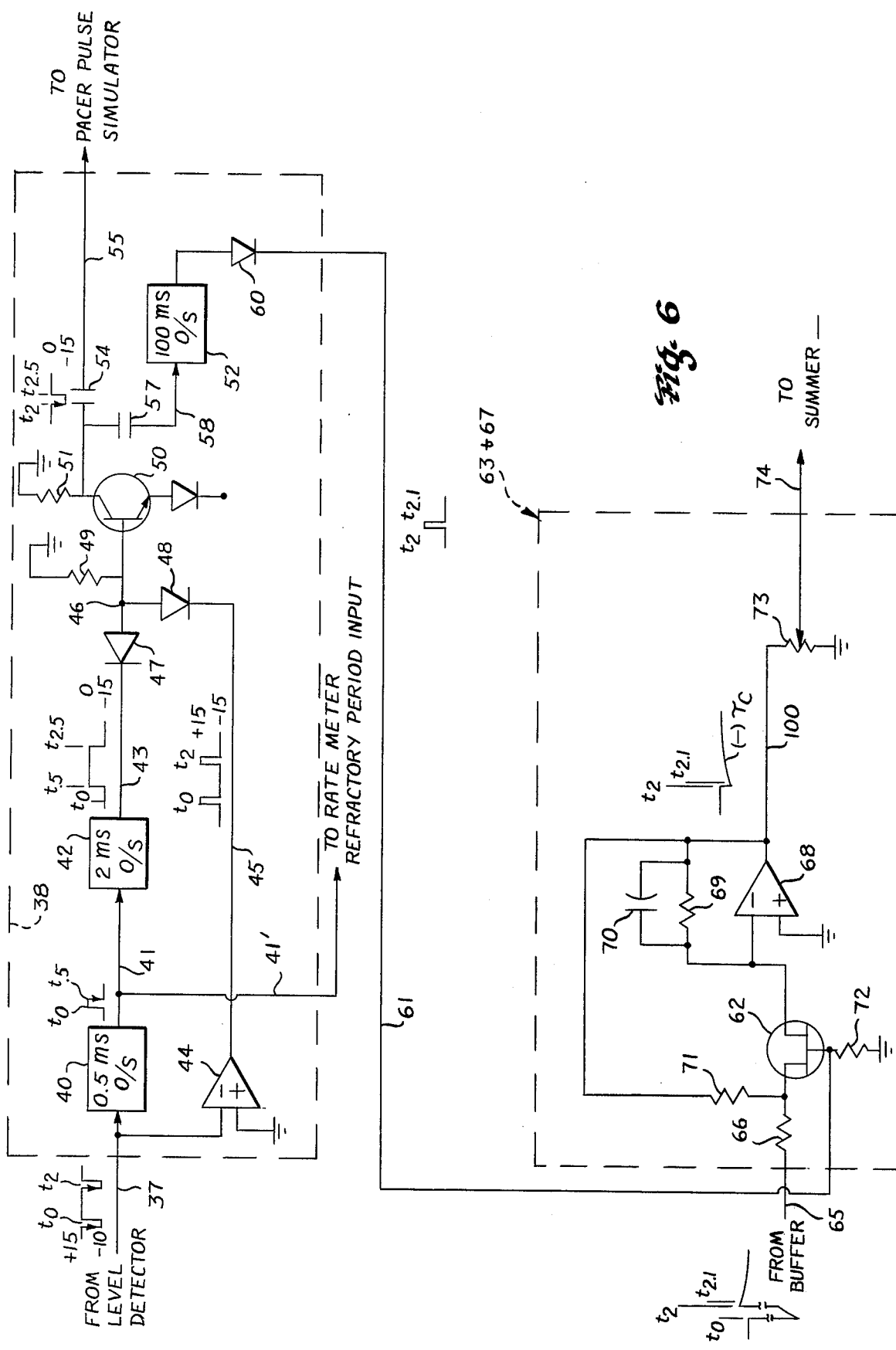
FIG. 6 is a functional schematic diagram depicting the pacer recharge waveform suppression circuitry of FIG. 5 in greater detail.
Figure 7:
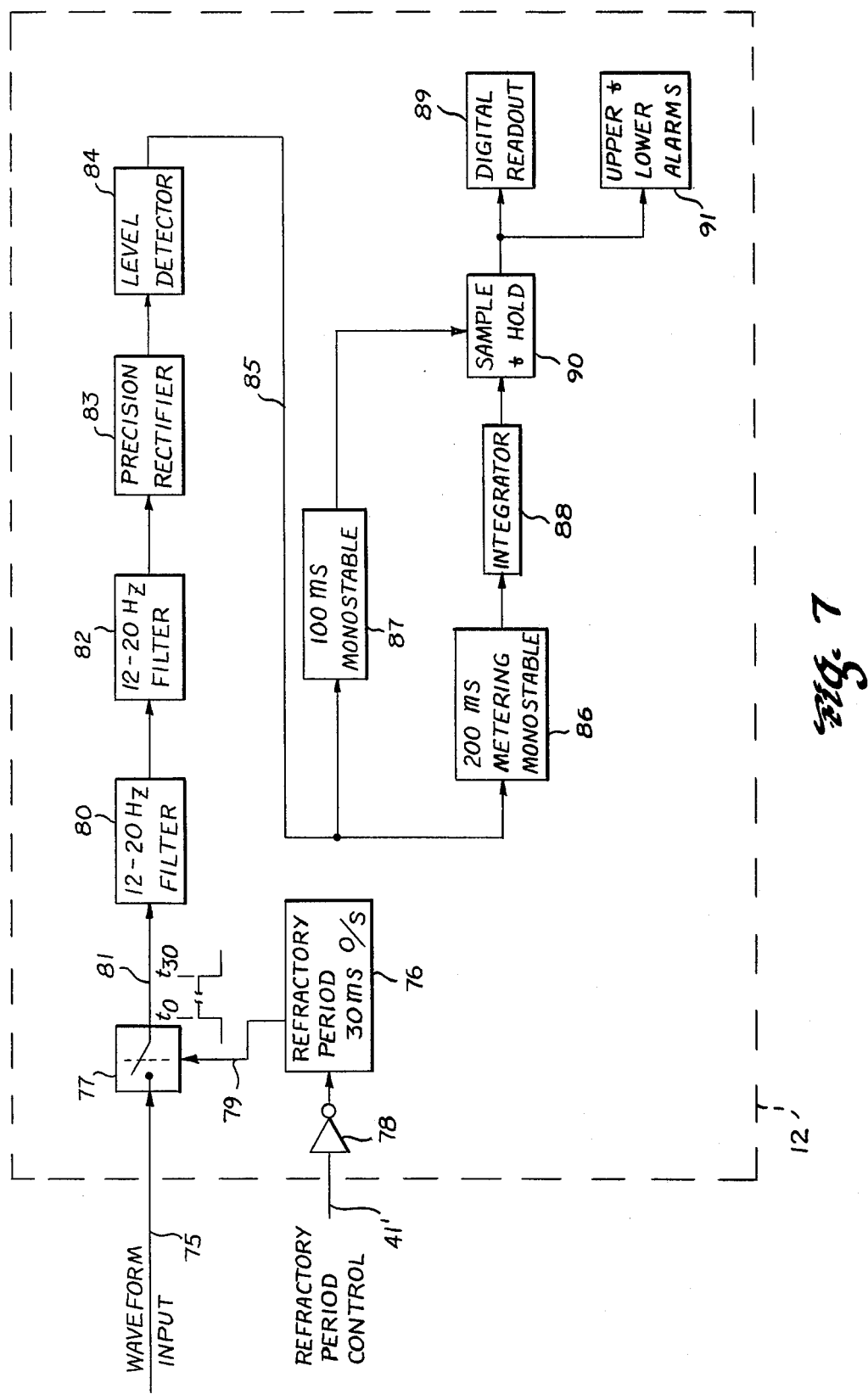
FIG. 7 is a functional block diagram depicting the heart rate meter of FIG. 1 in greater detail.

Referring to FIGS. 5–7, the patient electrode leads 16 are extended to inputs of an instrumentation amplifier 23 having its output extended through decoupling amplifier 24 to the input of a voltage controlled oscillator 25. A conventional baseline restoration circuit 26 is connected to provide feedback from the output of decoupling amplifier 24 to its input to minimize signal offset resulting from electrode unbalance. Amplifiers 23 and 24, voltage controlled oscillator 25, and additionally the transmitting side of optical coupler 27 are powered by a floating power supply 99 to provide the required patient isolation from the remaining circuitry which is connected to a grounded power supply (not shown). The VCO 25 operates at approximately 100 KHz and serves to frequency-modulate the sensed ECG signal, which frequency-modulated signal is then passed through the optical coupler 27 and is then brought to a ground reference in a known manner by phase locked loop 28 connected to the receiver output of optical coupler 27. Thus, the signal appearing at the output 29 of the phase locked loop 28 is a ground-referenced, amplified replica of the ECG signal sensed by electrode 17.

The signal appearing at the output 29 of phase locked loop 28 travels along two paths. In one path the sharp discharge pulse DP of the pacemaker is attenuated by high frequency suppression circuitry 30 which may comprise a non-linear filter with a movable pole. The pole moves towards zero frequency with rising amplitude of the signal being processed. In other words, high frequency suppression circuitry 30 may comprise a rate limiter, scaled such that its output voltage may not change faster than some preestablished rate substantially less than the rate of change present in the spike of the pacer discharge pulse DP. The output of suppression circuit 30 appears on the conductor 31 extended to summers 32 and 33 respectively. The waveform illustrated adjacent conductor 31 illustrates a strongly suppressed pacer discharge pulse DP, but with the lower-frequency recharge waveform RW and any naturally occurring or stimulated QRS complex remaining substantially intact.

The second path of the sensed ECG signal from the output 29 of the phase lock loop 28 extends to the respective inputs of a band pass filter 34 and a notch filter 35. This path includes circuitry which identifies the occurrence of a pacer pulse and uses such identification to then generate a transient signal which is extended to the other input of summer 33 for arithmetically cancelling and thereby suppressing the recharge waveform RW appearing at the other input to that summer in accordance with the invention. Further, recognition of the pacer pulse serves to generate a simulated pacer pulse of predetermined duration for application to the other input of summer 32 to reinsert, in the output signal extended to an oscilloscope or recorder, an enhanced representation of the pacer discharge pulse DP previously removed from the signal appearing at the other input to that summer.

The bandpass filter 34 comprises a slew rate detector for detecting the slew rate of the discharge pulse portion DP of the pacer pulse. The filter 34 comprises a first RC network for obtaining the time derivative of the input waveform. A second RC network in filter 34 rejects high frequency components of the input signal, as might appear as a result of the 100 KHz of the VCO in the phase locked loop 28. Stated another way, bandpass filter 34 is scaled to pass and/or emphasize signals in the frequency range of the pacer discharge pulse DP while relatively attenuating those signal components of relatively higher and/or lower frequency content.

The output of bandpass filter 34, as represented by line 35 and the waveform appearing thereabove, is extended to the input of a level detector 36. Because of the differentiation of the signal by bandpass filter 34, the waveform appearing on line 35 experiences an abrupt negative transition of large magnitude at time $t_o$ and then abruptly reverses itself and crosses the zero reference to some intermediate positive level as capacitor C discharges into the patient's heart and subsequently, at time $t_2$ abruptly goes even more positive to an extreme and then quickly returns substantially to the zero reference level. Thus, the pacer discharge pulse DP is seen to result in a pair of large magnitude signal excursions of opposite polarities appearing on line 35 and corresponding with the start and end respectively of the pacer pulse.

The level detector 36 comprise a pair of complementary differential amplifiers having the signal on line 35 extended to a respective complementary input of each, with the other input of each amplifier being preset to a threshold level voltage $\pm Th$ which is normally only exceeded by the differentiated voltage excursions of the pacer discharge pulse DP appearing on line 35, the recharge waveform RW and/or the PQRST complex normally being less and not affecting the output of level detector 36.

The output of detector 36, as represented by line 37 and the waveform illustrated thereabove, is extended to the input of pacer pulse duration detection circuitry 38. It will be noted in viewing the waveform illustrated above line 37 in FIG. 6 that the output of level detector 36 is normally at a positive voltage (i.e. + 15 volts) and makes a first abrupt negative step (i.e. −10 volts) of brief duration (i.e. 0.1 msec) at time $t_o$ when the threshold $-Th$ is exceeded and a second identical brief negative step at $t_2$ when the threshold $+ Th$ is exceeded.

The pacer pulse duration detector 38 is essentially comprised of a first delay monostable or one-shot 40, a second one-shot 42 for establishing duration of the pacer pulse detection interval, and coincidence detection circuitry including transistor 50 for providing a response when the second negative step or pulse on line 37 (normally occurring at time $t_2$) occurs within the interval defined by one-shot 42. A one-shot 52 for generating a sampling pulse or strobe signal is also shown as part of the detector circuitry 38, though it might alternatively have been shown as part of the sample-and-hold circuitry to be later discussed.

The output from level detector 36 is supplied, via line 37, to the trigger input of one-shot 40. One-shot 40 responds to the negative-going step of the trigger signal to provide a positive going output pulse whose duration is 0.3 msec. The output of one-shot 40 is extended, via line 41, to the trigger input of one-shot 42 and additionally via line 41' to rate meter 12. One-shot 42 is responsive to the negative-going signal on line 41 occurring at $t_3$ to generate a respective positive-going pulse having a duration of about 2.2 msec. at its output. Thus, the output of one-shot 42, as represented by line 43 and the waveform thereabove, is normally at a negative potential (i.e. −15 volts) and steps positively to a neutral or ground voltage at time $t_3$, remaining at this relatively higher voltage for 2.2 msec. until time $t_{2.5}$ whereupon it downsteps to the normal negative voltage. This pulse appearing on line 43 defines the pacer pulse detection interval or "window" with which the up-step in voltage of the signal appearing on line 37 must coincide for an indication that a pacer discharge pulse DP has occurred.

The signal from level detector 36 on line 37 is applied to the inverting input of an operational amplifier 44, the output of which is represented by line 45 and the waveform thereabove and is substantially the input signal inverted, except that the minus voltage swing is somewhat greater, i.e. +15 volts to −15 volts. The output of one-shot 42 and the output of amplifier 44 are respectively extended to a common junction 46 through diodes 47 and 48 respectfully. The anodes of diodes 47 and 48 are both connected directly to junction 46 such that the voltage appearing thereat is the lowest (most negative) of the two voltages appearing at any moment on lines 43 and 45 respectfully.

The voltage appearing at junction 46 is extended to the base of transistor 50 which is also connected to ground through base resistor 49. The emitter of transistor 50 is connected to a negative voltage (i.e. −15 volts) and the collector is connected through load resistor 51 to ground. Transistor 50 is turned on only when the voltage appearing on its base is more positive (i.e. ground) than the negative potential appearing at its emitter. Inasmuch as the output of one-shot 42 is normally at −15 volts, the transistor 50 will normally be turned off.

However, the signal on line 43 does increase to ground level during the interval $t_3 - t_{2.5}$. It will be noted that throughout most of that interval the signal appearing on line 45 is at −15 volts and accordingly determines the potential at junction 46, however at the end of the discharge pulse DP, at time $t_2$, the voltage on line 45 steps briefly to +15 volts such that the zero or ground voltage on line 43 now determines the potential appearing at junction 46. At this latter instant transistor 50 is switched into conduction causing the voltage appearing at its collector to drop from ground to the negative potential (−15 volts) of the emitter for the remaining time (i.e. 0.5 msec.) during which the signal on line 43 remains at ground.

The collector of transistor 50 is extended through coupling capacitor 54 via line 55 to the input of a pacer pulse simulator one-shot 56. Similarly, the output of collector 50 is extended though coupling capacitor 57 via line 58 to the trigger input of the 100 microsecond one-shot 52. Both one-shots 56 and 52 are responsive to the downstep in transistor collector voltage occurring at time $t_2$ for triggering the respective one-shots. The triggering of one-shot 52 results in the generation of a positive pulse whose duration is 100 microseconds, from time $t_2$ to $t_{2.1}$, and comprises the strobe pulse for sampling the voltage of the sensed ECG signal substantially at the beginning of the pacer recharge waveform RW. The strobe pulse from one-shot 52 is extended through diode 60 via line 61 to the gate of field effect transistor (FET) 62 comprising part of the trailing edge sample-and-hold circuitry 63.

The notch filter 35 receives the sensed ECG waveform signal at its input from the output of phase lock loop 28 and serves to reject 100 KHz components of the signal appearing as a result of the effects of the voltage control oscillators. The output of notch filter 35 essentially comprises an amplified version of the pacer pulse and/or PQRST waveform sensed by electrodes 17, which signal is then extended through buffer 64 and via line 65 to one end of input resistor 66 having its other end connected to the source electrode of FET 62.

The trailing edge sample-and-hold circuit 63 and the inverse transient generator 67 of FIG. 5 are illustrated in FIG. 6 as being principally comprised of FET switch 62, an operational amplifier 68, a parallel RC network of resistor 69 and capacitor 70 connected in feedback arrangement between the output and the inverting input of operational amplifier 68, and also a multiplier resistor 71. The drain electrode of FET 62 is extended to the inverting input of operation amplifier 68 and the multiplier resistor 71 extends from the output of amplifier 68 to the source electrode of FET 62. A gate resistor 72 extends from the gate of transistor 62 to ground.

The FET 62 is normally biased into nonconduction and the application of a positive-going strobe pulse to its gate from one-shot 52 switches the transistor into conduction for the 100 microseconds duration of the strobe pulse. During the brief conduction of FET 62, corresponding with $t_s$ in FIG. 4, the initial portion of the recharge waveform RW appearing on input line 65 is samples, with an inverse voltage proportional thereto then appearing at the output of amplifier 68 and serving to charge capacitor 70.

If it is assumed from FIG. 4 that the magnitude of the input signal on line 65 corresponds with the voltage $e_4$ at time $t_2$, the magnitude of the inverse voltage stored in capacitor 70 at the termination of the 100 microsecond sampling interval will equal $-e_4(R1/R2)$, where R1 equals the resistance of multiplier resistor 71 and R2 equals the resistance of resistor 66. The value of multiplier resistor 71 is greater (preferably twice) that of resistor 66 such that the magnitude of the inverse charge stored on capacitor 70 is greater than (preferably about twice) the magnitude of the voltage $e_4$ at the beginning of the recharge waveform RW, for a purpose to be hereinafter explained. The resistances of resistor 66 and 71 are preferably small, on the order of hundreds of ohms, in order that the substantially greater resistance (i.e. 1–10 megohm) of resistor 69 does not enter into the multiplier relationship. Capacitor 70 serves as an integrator of the voltage applied to the input of amplifier 68 and accordingly retains an inverse sample of at least (and preferably twice) the magnitude of the initial $e_4$ voltage of the recharge waveform RW at the end of the sampling strobe pulse.

Immediately on completion of the strobe pulse at time $t_{2.1}$, the FET 62 ceases conduction thereby disconnecting input resistor 66 and multiplier resistor 71 from the circuit, then only comprised of operational amplifier 68 and the parallel feedback network of resistor 69 and capacitor 70. With no additional input to amplifier 68, the charge stored on capacitor 70 begins a slow decay determined by the RC time constant of capacitor 70 and resistor 69. This time constant, designated $-\tau_c$, should correspond substantially with the recharge time constant $\tau_c$ of the recharge waveform RW. In other words, the time constant may be established such that the inverse transient suppression signal resulting at the output of amplifier 68 decays from a relatively negative voltage toward zero with about the same constant (i.e. 200–300 msec.) as for the decay of the recharge waveform RW. For instance, if resistor 69 has a value of about 10 megohms, capacitor 70 might have a value of about 0.02–0.03 microfarads.

The output of amplifier 68 is extended via line 100 to one end of a potentiometer 73 having its other end connected to ground. The center tap of potentiometer 73, represented by line 74, is extended to an input of summer 33. The inclusion of the potentiometer 73 in the inverse transient generator circuit 67 allows for magnitude adjustment of the generated inverse transient signal for adjustably optimizing its compensating offset with the recharge waveform RW of a particular patient. Inasmuch as the potentiometer 73 provides for scaling down the magnitude of the inverse transient signal, it is thus evident why the magnitude of the voltage stored on capacitor 70 is preferably greater than the corresponding magnitude of voltage exhibited by the recharge waveform RW.

It will be remembered that the signal extended via line 31 to the other input of summer 33, although having the pacer discharge pulse DP strongly suppressed, still retains a recharge waveform RW in its original form. By arithmetically summing the inverse transient signal appearing on line 74 with the signal appearing on line 31, the output of summer 33 as represented by line 75 and the waveform thereabove is seen to exhibit a substantial suppression of both the pacer discharge pulse DP and the recharge waveform RW such that substantially the only remaining signal having an amplitude and/or frequency composition characteristic of a QRS complex is, in fact, a QRS signal.

Reference is made now to FIG. 7 which illustrates the heart rate meter 12 in greater detail. With the exception of the refractory period one-shot 76 and the input control switch 77, the remaining circuitry of heart rate meter 12 employs known concepts and techniques for responding substantially only to signals in the 12-20 Hz frequency range of the QRS complex of a heart beat signal. However, such circuits, while being essentially frequency selective, may be overloaded by a signal of particularly large magnitude outside the band pass frequency of the system, as for instance the pacer discharge pulse.

The pulse from one-shot 40 in amplifier 11 is extended via line 41 through an inverter 78 to the trigger input of 30 msec. one-shot 76. One-shot 76 is triggered by a negative-going step, thus the inverter 78 provides for triggering one-shot 76 during the positive step of one-shot 40 at $t_o$. The output of one-shot 76 provides a positive pulse at 30 msec. duration extended via line 79 to the control input (gate) of switch 77. Switch 77 may typically be a junction field effect transistor (JFET) which is normally closed or conducting. The signal appearing on line 75 is extended to one terminal of the JFET switch 77, with the remaining terminal being connected via line 81 to the input of a first 12-20 Hz bandpass filter 80. The refractory period one-shot 76 is operative to block conduction of JFET switch 77 for a predetermined period (i.e. 30 msec.) beginning at time $t_o$, thereby to prevent the signal on line 75 from appearing at the input of filter 80.

The predetermined refractory period is preferably selected to be long enough to coincide with the discharge pulse portion DP of a pacer pulse and the early portion of the recharge waveform RW, however it must not be so long that it inhibits the passage of a QRS complex to the filter 80 resulting from the capture of the heart by the simulation pulse. Thus, because the refractory period interval may only be on the order of 20 – 30 msec., there exists the need, met by the invention, for suppressing the remaining portion of the recharge waveform RW which is of a magnitude capable of registering a response in the circuitry of meter 12.

Further, although the JFET switch 77 effectively blocks almost all of the discharge pulse DP from the rate monitoring circuitry, it exhibits sufficient capacitance to have passed a portion of the pacer spike had such spike not otherwise been suppressed by the high frequency suppression circuit 30 of FIG. 5. Furthermore, the high frequency suppression circuit 30 serves to suppress the high amplitude pacer spike occurring precisely at $t_o$ inasmuch as the response of level detector 36, and accordingly delay one-shot 40 and refractory period one-shot 76, are in fact slightly delayed (i.e. 0.1 msec) from the $t_o$ instant in time.

Bandpass filter 80 is followed by a second 12-20 Hz bandpass filter 82. Filters 80 and 82 act as ringing filters which yield an oscillotory burst for each QRS complex. The output of filter 82 is extended to the input of a precision rectifier 83 which converts this oscillotory burst into a unipolar burst which represents, in unipolar fashion, the relative positive and/or negative magnitudes of the QRS complex. The use of rectifier 83 permits R-waves of either polarity to be detected.

The monopolar burst from the output of rectifier 83 is extended to the input of level detector 84 which will change states only if the unipolar burst exceeds some predetermined threshold amplitude indicative of an R-wave. When level detector 84 does change states this is taken as an indication that an R-wave does exist and accordingly results in an output pulse extended along line 85 to the respective trigger input of a 200 msec. metering monostable (one-shot) 86 and a 100 msec. monostable (one-shot) 87.

The 200 msec. output pulse from monostable 86 represents a predetermined standard unit of energy which is extended to the input of an integrator 88 wherein it is integrated with 200 msec. pulses resulting from previous recognitions of the QRS complex such that the integrated sum is representative of the average heart rate. The output of integrator 88 may then be used as the input to either analog or digital readout means. In the illustrated embodiment, the output of integrator 88 is fed to a digital readout 89 through conventional sample and hold circuitry 90.

The 100 msec monostable 87 is utilized to generate a sampling pulse which is extended to the strobe input of sample-and-hold circuit 90. The strobe pulse from monostable 87 is timed such that it occurs substantially midway in the 200 msec. interval of the metering pulse from monostable 86. The use of a sample-and-hold circuit 90 intermediate the output of integrator 88 and the readout means serves to reduce the annoying fluctuations of average pulses on an analog meter and to make a digital panel meter useful. The sampling of the output of integrator 88 during the mid-portion of the 200 msec. metering pulse interval is further helpful in this respect. The signal appearing at the output of sample-and-hold circuit 90 is additionally illustrated as being extended to upper and lower alarm circuits 91 for providing a visual, audible, and/or other type of alarm if the heart rate exceeds some preset upper or lower limit.

Referring back to FIGS. 5 and 6, it will be recalled that the pacer pulse recognition circuitry additionally provided a trigger pulse to the trigger input of pacer pulse simulator one-shot 56 via line 55 whenever a pacer pulse has been recognized. The simulator 56 provides an output pulse of predetermined polarity and duration, in this instance a negative pulse of 15 msec. duration, for use in simulating a pacer pulse in an oscilloscope or recorder display. Although a signal having such pacer pulse present might have been obtained at point 29 at the output of phase locked loop 28, the slew rate and duration of such pacer spike are normally so fast and short as to prevent accurate tracking by the stylus of a recorder. Accordingly, simulator 56 provides a simulated pacer signal having significantly greater duration than the natural pacer spike (i.e. 51 msec. vs. 2 msec.) The output of the simulator one-shot 56, as represented by line 95 and the waveform thereabove, is extended to the other input of summer 32 for arithmetic with the signal appearing on line 31. The output of summer 32, as represented by the line 36 and the waveform thereabove, comprises the informational input signal extended to the display means 14. In this way, the occurrence of a pacer spike may be clearly recorded on an oscilloscope or permanent recorder by using a standardized and easily recorded simulated pacer signal. Although the simulated pacer signal beings at time $t_2$, or in other words 2 msec. after the beginning of the actual pacer spike, such difference in timing is virtually imperceptable to the eye.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

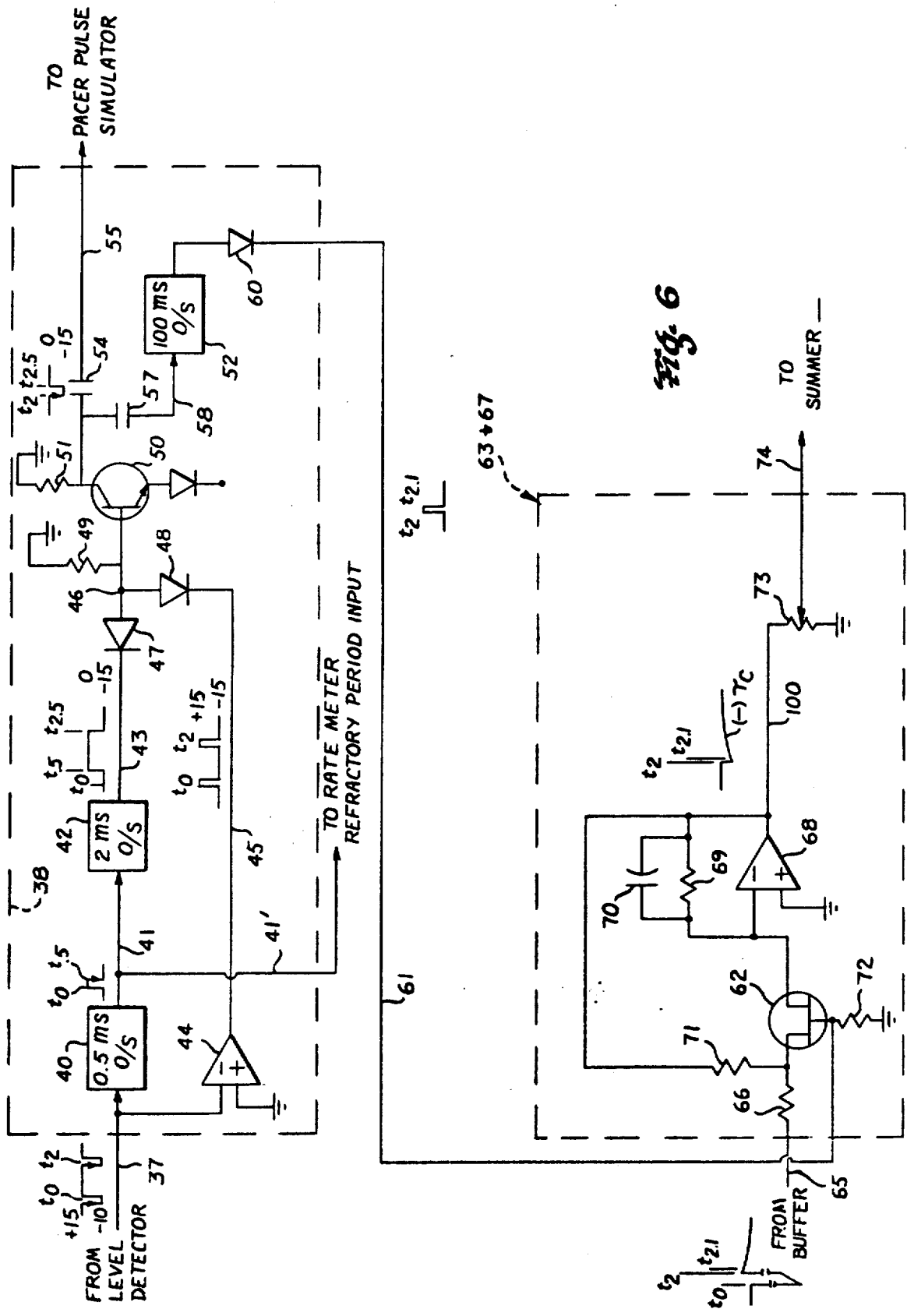

We claim:

1. In a heart monitoring system including means for sensing a patient's ECG signals, means responsive to the QRS complex of sensed ECG signals for indicating the patient's heart rate, and signal suppression means for suppressing the pacer discharge pulse portion of a heart pacer signal artifact possibly appearing in the sensed ECG signal to prevent false actuation of the heart rate indicating means thereby, the pacer signal artifact being comprised of the pacer discharge pulse portion and a recharge waveform portion, the improvement wherein said suppression means additionally incudes:

means responsive to a pacer signal artifact in the sensed ECG signal for generating a recharge waveform suppression signal of opposite polarity to the recharge waveform portion of the pacer signal, and means for arithmetically summing the recharge waveform suppression signal with the sensed ECG signal to additionally suppress said recharge waveform portion, the magnitude and duration of said recharge waveform suppression signal being such as to thereby also prevent false actuation of the heart rate indicating means by said recharge waveform portion of the pacer signal artifact.

2. The heart monitoring system of claim 1 wherein the magnitude of said recharge waveform suppression signal is substantially proportional to the magnitude of the respective recharge waveform portion of the pacer signal.

3. The heart monitoring system of claim 2 wherein said recharge waveform portion of the pacer signal has a magnitude sufficient for a particular interval to actuate the heart rate indicating means and wherein said recharge waveform suppression signal exists at least for an interval substantially concurrent with said particular interval of said recharge waveform portion.

4. The heart monitoring system of claim 2 wherein the magnitude of said recharge waveform suppression signal is substantially equal to the magnitude of the respective recharge waveform portion of the pacer signal.

5. The heart monitoring system of claim 1 wherein said suppression means includes means responsive to a pacer signal artifact for generating a strobe signal substantially at the beginning of the recharge waveform portion thereof and said recharge waveform suppression signal generating means comprises a transient generator providing an output signal the magnitude of which is a function of the magnitude of the input signal applied thereto, and switch means responsive to said strobe signal for extending said beginning of said recharge waveform portion of the pacer signal artifact to said transient generator as said input signal thereto.

6. The heart monitoring system of claim 5 wherein said recharge waveform portion of said pacer signal artifact is an exponential charging function having a particular time constant and said transient generator comprises an RC circuit, the value of said RC circuit being selected to provide an exponential decay of the opposite polarity as said input signal with a time constant which corresponds substantially with said particular time constant of said exponential charging function of said recharge waveform portion.

7. The heart monitoring system of claim 6 wherein said RC circuit comprises parallel-connected resistance means and capacitance means, said parallel-connected resistance means and capacitance means being connected in series with said switch means and said summing means.

8. The heart monitoring system of claim 5 wherein said strobe signal generating means comprises means for obtaining a representation of the time derivative of the sensed ECG signal including any possible pacer, the timer derivative representation of a pacer discharge pulse including first and second spikes of opposite polarities at the beginning and end respectfully of the pacer discharge pulse, means responsive to said time derivative representation for providing a trigger signal each time the magnitude of the time derivative representation exceeds a threshold corresponding with the respective opposite polarities of the time derivative representation, the threshold for each polarity being selected such that a first trigger signal is provided at the start of a pacer discharge pulse and a second trigger signal is provided at the end of a pacer discharge pulse, means responsive to said first trigger signal for initiating a predetermined timing interval following a predetermined delay, the termination of a normal pacer discharge pulse occurring during said timing interval, and means responsive to said second trigger signal occurring during said predetermined interval for generating said stroke pulse.

9. The heart monitoring system of claim 8 wherein the thresholds respectively corresponding with the opposite polarities of said time derivative representations are substantially equal, said thresholds being representative of a minimum slew rate of said sensed signal including any possible pacer discharge pulse.

* * * * *

UNITED STATES PATENT AND TRADEMARK OFFICE
CERTIFICATE OF CORRECTION

PATENT NO. : 4,105,023
DATED : August 8, 1978
INVENTOR(S) : Thomas F. Marchese
Rauf S. Argon It is certified that error appears in the above-identified patent and that said Letters Patent are hereby corrected as shown below:

In claim 8, line 5, delete "timer" and insert --time--;

In claim 8, line 23, delete "stroke" and insert --strobe--;

In the drawings, cancel one of the duplicate Sheets 2 of 4 and substitute Sheet 3 of 4 (Fig. 6) as shown on the attached sheet.

Signed and Sealed this

Sixth Day of March 1979

[SEAL]

Attest:

RUTH C. MASON
Attesting Officer

DONALD W. BANNER
Commissioner of Patents and Trademarks